US00PP29717P3

(12) United States Plant Patent
Olesen

(10) Patent No.: US PP29,717 P3
(45) Date of Patent: Oct. 2, 2018

(54) MINIATURE ROSE PLANT NAMED 'POULPAH088'

(50) Latin Name: ***Rosa* hybrid**
Varietal Denomination: Poulpah088

(71) Applicant: Mogens Nyegaard Olesen, Fredensborg (DK)

(72) Inventor: Mogens Nyegaard Olesen, Fredensborg (DK)

(73) Assignee: POULSEN ROSE A/S, Fredensborg (DK)

( * ) Notice: Subject to any disclaimer, the term of this patent is extended or adjusted under 35 U.S.C. 154(b) by 0 days.

(21) Appl. No.: 15/330,300

(22) Filed: Sep. 6, 2016

(65) Prior Publication Data

US 2018/0070496 P1 Mar. 8, 2018

(51) Int. Cl.
*A01H 5/02* (2018.01)

(52) U.S. Cl.
USPC ..... Plt./118
CPC ..... *A01H 5/0222* (2013.01)

(58) Field of Classification Search
USPC ..... Plt./101, 116, 118
See application file for complete search history.

(56) References Cited

PUBLICATIONS

UPOV-PLUTO: Plant Variety Database, Oct. 20, 2017, citation for Poulpah088. 1 page.*
Poulsen—Outdoor Roses 2015. http://fliphtml5.com/kekq/iswp/basic. Accessed Oct. 20, 2017. 5 pages.*

* cited by examiner

*Primary Examiner* — Susan McCormick Ewoldt
*Assistant Examiner* — Karen M Redden

(57) ABSTRACT

A new garden rose plant of the Miniature class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah088'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpah088', originated as a single seedling from the stated cross.

The new variety may be distinguished from its male pollen parent and female seed parent primarily by the following characteristics. The male pollen parent plant has apricot blend flower color, while the new variety has yellow flowers. The female seed parent plant has apricot blended flower color, while the new variety has yellow flowers.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah088' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpah088' was selected in the spring of 2008 by the inventor as a single plant from the progeny of the aforementioned hybridization.

Asexual reproduction of 'Poulpah088' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpah088' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah088'.

Specifically illustrated in FIG. 1 of the drawings are open flowers at various stages of development, petals detached, sepals detached, and reproductive flower parts.

Figure 1:
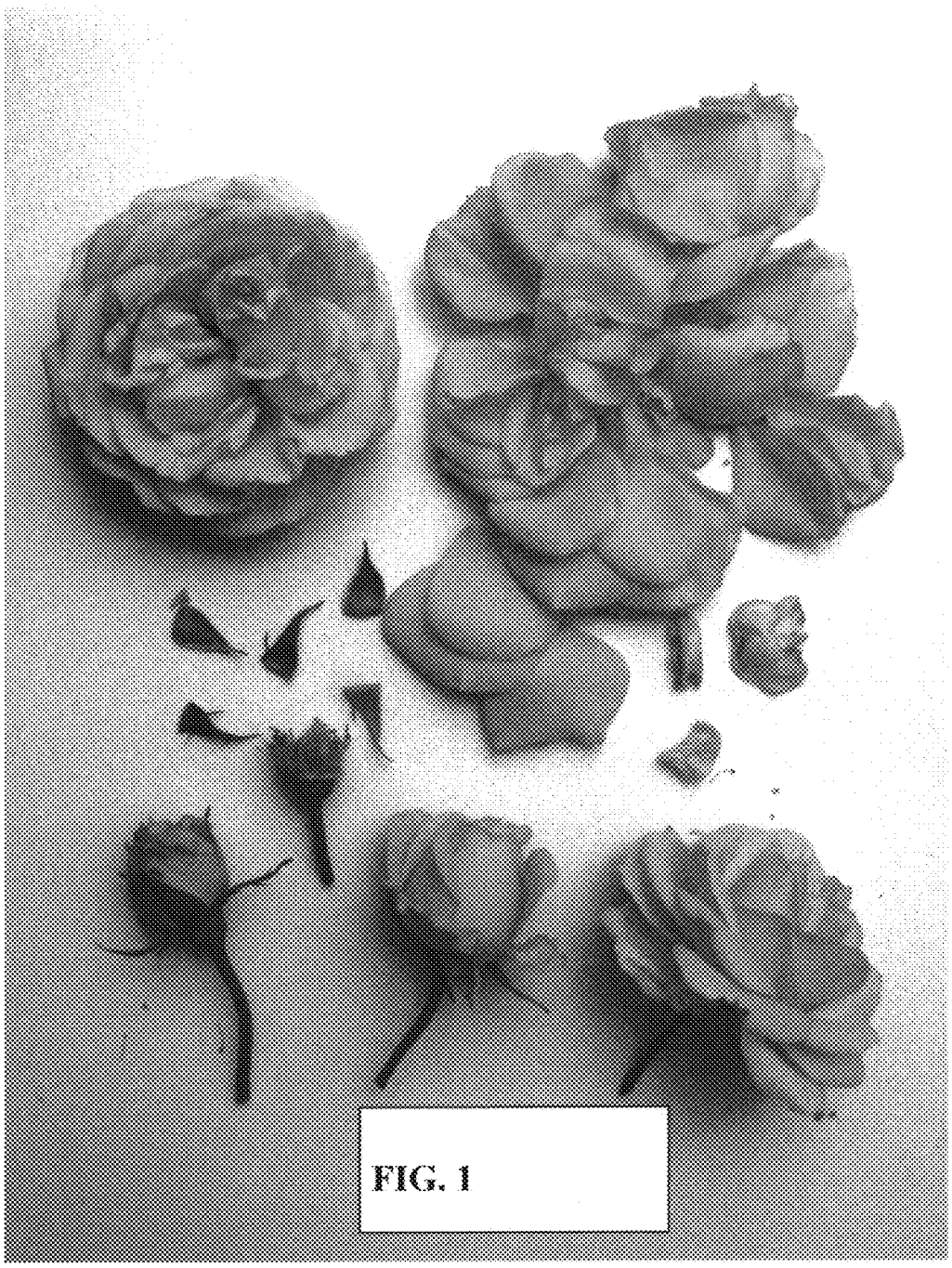
Figure 2:
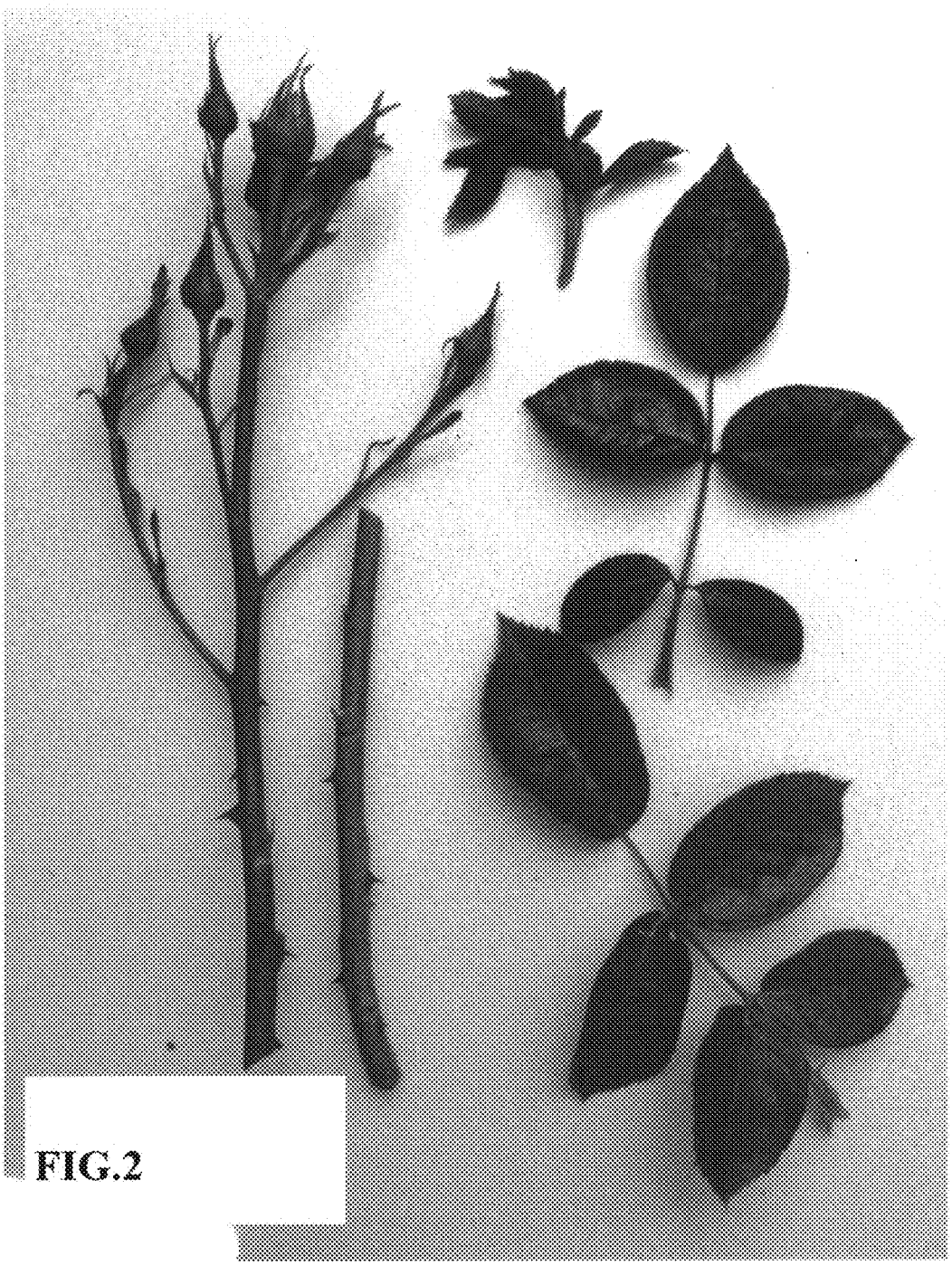

Illustrated in FIG. 2 are leaves, bare stems, and a cluster of flower buds on a branch. Plants shown are 2 years of age.

DETAILED DESCRIPTION OF THE VARIETY

The following is a description of 'Poulpah088', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulsun', U.S. Plant Pat. No. 9,716 are compared to 'Poulpah088' in Chart 1.

CHART 1

| | 'Poulpah088' | 'Poulsun' |
|---|---|---|
| Petal Count | 70 | 30 to 35 |
| Flower Diameter | 90 mm | 50 to 63 mm |
| Upper petal surface color | Yellow Group 10A | Yellow Group 13A |

FLOWER AND FLOWER BUD

Blooming habit: Continuous.

Flower bud:

*Size.*—Upon opening, 20 mm in length from base of receptacle to end of bud. Bud diameter is 15 mm.

*Bud form.*—Ovoid.

*Bud color.*—As sepals divide petals are Yellow-Orange Group 15B with intonations of Orange Group 29A.

*Sepal inner surface.*—Color: Yellow-Green Group 147D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have light foliaceous appendages on three of the five sepals.

*Sepal size:* 25 mm long, 10 mm wide.

*Receptacle.*—Texture: Smooth. Size: 10 mm in height, 10 mm wide. Color: Yellow-Green Group 144A. Shape: Campanulate.

*Pedicel.*—Surface: Smooth. Length: 40 mm. Diameter: 4 mm on average. Color: Yellow-Green Group N144B. Strength: Strong.

*Peduncle.*—Length: 1 to 3 cm. Diameter: About 4 mm. Color: Yellow-Green Group 144A. Texture: Smooth.

Flower bud development: Flower buds are borne in clusters of 5 to 7 flower buds per stem in panicle form.

Flower bloom:

*Fragrance.*—Light.

*Duration.*—The blooms have a duration on the plant of approximately 10 days. Petals fall cleanly away from plant after flowers have fully matured.

*Size.*—Flower diameter is 90 mm when open. Flower depth is 45 mm.

*Flower shape.*—Rosette, very double flower with many slightly overlapping petals of different sizes.

*Shape of flower, side view.*—The upper portion is convex. Flat on lower portion.

Petalage: Under normal conditions, flowers have 70 petals total.

General tonality of flower: Open flowers are Yellow Group 10A.

Petal color:

*Upon opening, inner and outer petals.*—Upper surface: Yellow Group 10A. Lower surface: Yellow Group 10C with intonations of Yellow-Orange Group 16C.

*Basal petal spots, upon opening.*—No distinctive coloration.

Petals:

*Petal reflex.*—Strong to moderate reflex.

*Margin.*—Entire and uniform. Moderate undulations.

*Shape.*—Generally broad elliptical. Apex shape: Rounded. Base shape: Acute.

*Size.*—35 mm (l)×33 mm (w).

*Texture.*—Smooth.

*Thickness.*—Average.

Petaloids:

*Size.*—15 mm (l) by 10 mm (w).

*Quantity.*—About 10.

*Shape.*—Base is acute, apex is rounded.

*Color.*—Upper surface is Yellow Group 10A. Lower surface is Yellow Group 10C with intonations of Yellow-Orange Group 16C.

Reproductive flower parts:

*Pollen.*—None observed.

*Anthers.*—Size: 2 mm in length. Color: Yellow Group 8C. Quantity: 38 on average.

*Filaments.*—Color: Yellow Group 13A. Length: 4 mm.

*Pistils.*—Length: 4 mm. Quantity: 22 on average.

*Stigmas.*—Color: Greyed-Yellow Group 162B.

*Styles.*—Color: Green-White Group 157A.

*Location of stigmas.*—Inferior in location relative to the length of the filaments and the height of the anthers.

*Hips.*—None Observed.

PLANT

Plant growth: Upright, bushy. Plants are 40 cm in height, and 35 cm wide.

Stems:

*Color.*—Juvenile growth: Yellow-Green Group 144B. Mature growth: Yellow-Green Group 144A.

*Length.*—On average, canes are 20 cm from the base of the plant to the flowering portion.

*Diameter.*—6 mm.

*Internodes.*—On mature canes about 40 mm between nodes.

*Surface texture.*—Young wood: Smooth. Older wood: Smooth.

Long prickles:

*Incidence.*—5 prickles per 10 cm of stem.

*Size.*—Average length of prickles on mature stems is 5 mm.

*Shape.*—Upper portion is linear. Lower portion is concave.

*Color.*—Juvenile prickles: Greyed-Red Group 179B. Mature prickles: Greyed-Red Group 179B.

Plant foliage:

*Compound leaf.*—150 mm (l)×90 (w).

*Quantity.*—2 leaves per 10 cm of stem on average.

*Leaf bearing angle to the stem.*—45 degrees.

*Color of juvenile foliage.*—Upper side: Yellow-Green Group 144B with intonations of Greyed-Orange Group 176A. Lower side: Yellow-Green Group 144B.

*Color of mature foliage.*—Upper side: Yellow-Green Group 146A. Lower side: Yellow-Green Group 146B.

Plant leaves and leaflets:

*Stipules*.—Size: 18 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 40 mm. Diameter: 2 mm. Upper surface: Yellow-Green Group 144A. Lower surface: Yellow-Green Group 144A.

*Rachis*.—Length: 42 mm. Upper surface: Yellow-Green Group 144A. Lower surface: Yellow-Green Group 144A.

*Leaflet*.—Quantity: Normally 5 leaflets. Margins: Serrated. Size: On average terminal leaflets are 50 mm long, 38 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah088', substantially as illustrated and described herein, due to its abundant yellow flowers, disease resistance, and extended period of bloom.

* * * * *